United States Patent [19]

Norelli et al.

[11] Patent Number: 5,342,385
[45] Date of Patent: Aug. 30, 1994

[54] FLUID-EXPANDABLE SURGICAL RETRACTOR

[76] Inventors: Robert A. Norelli, 2412 N. Lehman Rd., Peoria, Ill. 61604; Edward H. Jelinek, 9930 Harney Pkwy. South, Omaha, Nebr. 68114; George E. Cullan, 110 W. 22nd Ave., Hutchinson, Kans. 67502

[21] Appl. No.: 914,712

[22] Filed: Aug. 14, 1992

Related U.S. Application Data

[63] Continuation of Ser. No. 650,771, Feb. 5, 1991, abandoned.

[51] Int. Cl.$^5$ .......................................... A61M 29/00
[52] U.S. Cl. .................................. 606/193; 604/104
[58] Field of Search ............... 606/191, 192, 193, 194, 606/195, 198, 202; 604/96, 278, 279, 104, 105, 106, 107; 600/31

[56] References Cited

U.S. PATENT DOCUMENTS

| | | | |
|---|---|---|---|
| 3,774,596 | 11/1973 | Cook | 128/5 |
| 3,817,242 | 6/1974 | Uddenberg | 128/20 |
| 3,853,120 | 12/1974 | Batista | 128/20 |
| 3,863,639 | 2/1975 | Kleaveland | 128/303 R |
| 3,882,852 | 5/1975 | Sinnreich | 128/4 |
| 4,117,847 | 10/1978 | Clayton | 128/348 |
| 4,274,398 | 6/1981 | Scott, Jr. | 128/20 |
| 4,718,151 | 1/1988 | LeVahn et al. | 24/535 |
| 4,747,393 | 5/1988 | Medwid | 128/120 |

Primary Examiner—C. Fred Rosenbaum
Assistant Examiner—Manuel Mendez
Attorney, Agent, or Firm—Zarley, McKee, Thomte, Voorhees & Sease

[57] ABSTRACT

A surgical retractor includes a generally annular bladder which is fluidly expandable so as to apply an outwardly-directed radial force against soft tissues. The inner and outer annular bladder walls are formed of a flexible resilient material with elastic properties to permit a variable amount of expansion in predetermined directions. A tube extending from the bladder connects the bladder to a three-way valve which is used to selectively inflate, by means of an attached pump, or to exhaust the bladder. A plurality of baffles within the bladder provide the retractor with a generally cylindrical shape. A woven fabric matrix is mounted to the inner annular wall to control expansion thereof. Pockets formed in the woven material permits the introduction of puncture- and incision-resistant shields to prevent accidental puncture of the bladder.

8 Claims, 6 Drawing Sheets

5,342,385

FLUID-EXPANDABLE SURGICAL RETRACTOR

This case is a continuation of application Ser. No. 07/650,771, now abandoned, filed Feb. 5, 1991.

TECHNICAL FIELD

The present invention generally relates to surgical retractors and relates more particularly to an improved retractor comprised of flexible material which can be applied in a contracted state and then fluidly pressurized with gas or liquid to achieve rigidity and thereby retraction of tissue.

BACKGROUND OF THE INVENTION

The customary and current techniques involved in surgical procedures of the abdomen, thorax, vagina, etc., often utilize rigid or semi-malleable metallic retractors applied to influence the position of tissues within and adjacent to the operative field. These traditional retractors are currently available in a plurality of sizes, shapes, and configurations, but the common thread appears to be the rigidity of the basic materials of construction. A problem with rigid retractors is that the unyielding nature of the construction material is responsible for neuronal impingement resulting in transient or residual deficits, pressure necrosis of soft tissue, incomplete hemostasis requiring additional efforts to achieve hemostasis (e.g., electric cautery), asymmetric retraction of soft tissue, as well as usually requiring a surgical assistant to physically hold the retractor by hand and thereby apply the tissue retracting force.

An attempt to avoid these and other problems can be seen in the retractor design refinements such as increasing the retractor-tissue interface areas and by introducing a curvature to the retractor blade. However, in practicality, the lateral edges of the rigid retractor blade still present a localized focus of high pressure against soft tissue. Also, since specific locations of the underlying sensitive structures, such as nerve fibers and blood vessels and lymphatic channels, are subject to extensive anatomic variation and as a result ultimately unknown, the surgeon must exercise the judgment and wisdom of experience to arrive at a "best-guess" location for application of the retractor blade to preferably avoid compression of these structures.

Other common problems of existing retractors are that they require a surgical assistant to hold the retractor. The use of a surgical assistant can be a problem in itself due to (1) fatigue of the assistant, (2) inaccurate placement of the retractor by the assistant as opposed to placement by the primary operator, and (3) suboptimum exposure within the operative field. Attempts to eliminate the need for a surgical assistant are embodied by rigid or malleable metallic retractor blades attached to self-retaining retraction frames, blades which are connected to surgical table accessories or preferentially to flexible/lockable retraction arms. The retractors, although partially or totally within the sterile operative field, nonetheless extend well beyond the general dimension of the incision site. The obvious detriments involve a reduction in the surgeon's access to the operative site due to interference by the external frameworks and the potential for visual obstruction by the frameworks when intra-operative complications necessitate a change in surgical approach. Furthermore, the ultimate tissue retraction is achieved by means of rigid or malleable metallic retractor blades, thereby inducing the previously mentioned problems with hemostasis, necrosis, neuronal impingement, etc.

It is therefore a general object of the present invention to provide an improved tissue retractor for operative procedures.

Another object is to provide a retractor manufactured of readily available materials and methods in an inexpensive and mass-producible manner.

Another object is to provide a retractor of a basic manufacturing design amenable to development into a complete system possessing versatility of size and shape, as well as the capability to address the interrelatedness and complexity of various surgical necessities, e.g., an internal cavity retractor with incorporated pouch to accept mobile organs such as bowel or omentum to protect against desiccation.

A further object is to provide a retractor which will be cost-effectively disposable to avoid the expense of sterilization and/or the risks of faulty sterilization.

Yet another object of this invention is to provide a retractor which will largely or totally contact the incision site.

A further object is to provide a retractor capable of being applied completely inside of a body cavity to control the location of internal organs and to improve visibility of the operative field.

Another object is to provide a retractor which will serve as a protective barrier when applied within a body cavity between internal organs and surgical instruments.

Yet another object is to provide a retractor which can be applied, adjusted, and maintained quickly, simply, and easily by a sole operator.

These and other objects will be apparent to those skilled in the art.

SUMMARY OF THE INVENTION

The surgical retractor of this invention includes at least one bladder which is fluidly expandable to apply an outwardly directed radial force against soft tissues, thereby achieving retraction of these tissues from the operative field. A plurality of bladder configurations may be employed.

The bladder walls are comprised of a flexible and durable material which have fibers oriented to influence the direction and extent of expansion and resiliency. Additional non-inflating pockets, loops, flaps and the like may be included in the construction.

Coupled to the bladder is a resilient, pressure-tolerant tube capable of conveying the fluid from the reservoir to the bladder.

DESCRIPTION OF THE PREFERRED EMBODIMENTS

Figure 1:
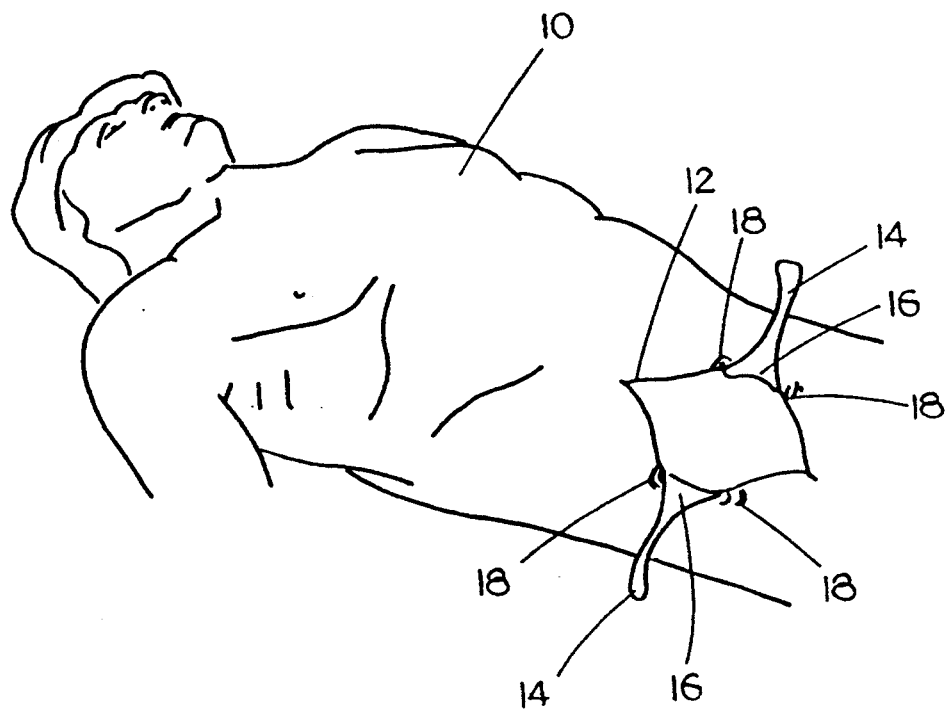
FIG. 1 is a perspective view of a patient utilizing prior art retractors in an incision.

Referring now to the drawings, in which identical or corresponding parts are identified with the same reference numerals, and more particularly to FIG. 1, a patient 10 with an abdominal incision 12 has a pair of prior art retractors 14 retaining the sides of the incision in a spaced-apart relation. Conventional retractors 14 include a large arcuate paddle portion 16 which holds the incision sides. However, since the retractors are formed of a rigid material, high pressure exists at each edge of the paddle portions where the incision sides are retained by the paddle portions, identified generally at 18. These high pressure points can cause pressure necrosis of soft tissue, as well as other problems, as discussed hereinabove.

Figure 2:
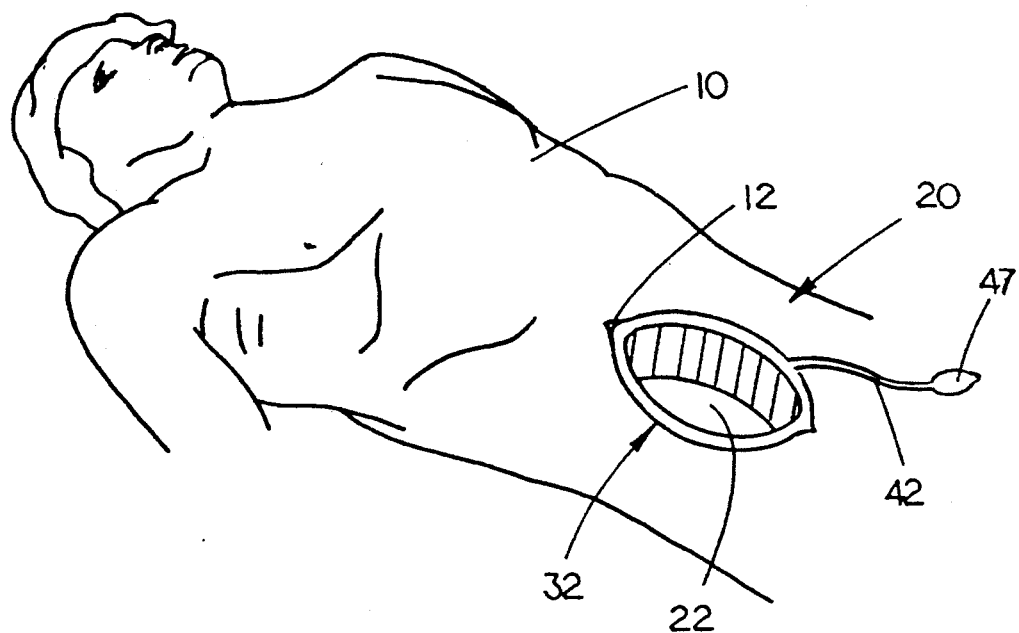
FIG. 2 is a perspective view of a patient utilizing the retractor of the present invention within an incision.
Figure 3:
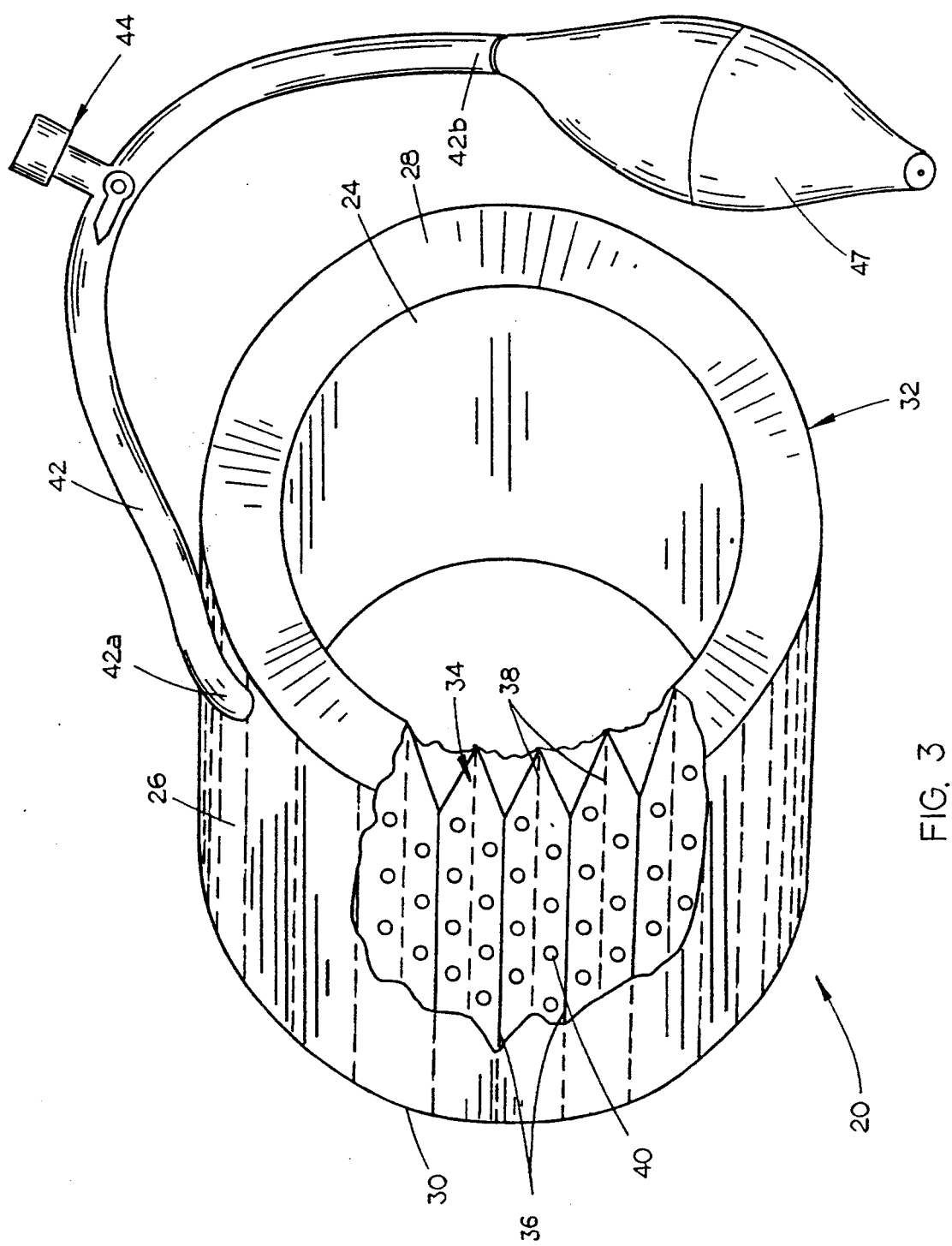
FIG. 3 is an enlarged perspective view of the present invention, with a portion broken away for a view of the interior.

Referring now to FIG. 2, patient 10 has an abdominal incision 12 with the retractor 20 of the present invention operably mounted therein to retain the incision sides in a spaced-apart relation to provide a free and clear work area, designated generally at 22. As shown in FIG. 3, retractor 20 is a generally cylindrical-shaped annular member having an inner annular wall 24, an outer annular wall 26, a forward end wall 28 and a rearward end wall 30. Forward and rearward end walls 28 and 30 are generally ring-shaped so as to form a seal between inner and outer annular walls 24 and 26 to form a sealed bladder 32. A plurality of baffles 34 extend between inner and outer annular walls 24 and 26 and between forward and rearward end walls 28 and 30 within bladder 32. Baffles 34 have their outer longitudinal edges 36 affixed to outer annular wall 26, and their inner longitudinal edges 38 affixed to inner annular wall 24, with pairs of outer edges 36 and pairs of inner edges 38 abutting one another to form a zigzag or accordion space. The accordion shape permits the bladder 32 to be collapsed to a very small diameter while affording structural strength to the bladder 32 while in the inflated mode, as described in more detail hereinbelow. A plurality of apertures 40 are formed in baffles 34 to permit fluid flow throughout the entire bladder 32.

A flexible tube 42 is fluidly connected at one end 42a to bladder 32, to introduce and exhaust fluid from bladder 32. An adjustable valve 44 is interposed in tube 42 between ends 42a and 42b. Valve 44 is fully adjustable to adjust the flow rate of fluid into and out of bladder 32, and is adjustable to prevent the entire flow of fluid. A fluid pump 47 is connected to end 42b of tube 42, and is designed to pump fluid through tube 42 into bladder 32.

As shown in FIG. 2, retractor 20 is inserted within incision 12, and air is then pumped into bladder 32 via tube 42 and pump 47. Preferably, tube 42 is connected to bladder 32 adjacent forward end wall 28 such that tube 42 may drape over the patient's body with minimal contact to incision 12. As air is pumped into bladder 32, baffles 34 (FIG. 3) will extend and bladder 32 will become generally rigid to hold the outside edges of incision 12 in a manner providing a central opening (donut hole) through which the surgeon gains access to the operative field. By opening valve 44, retractor 20 may be deflated and removed from the incision.

Figure 4:
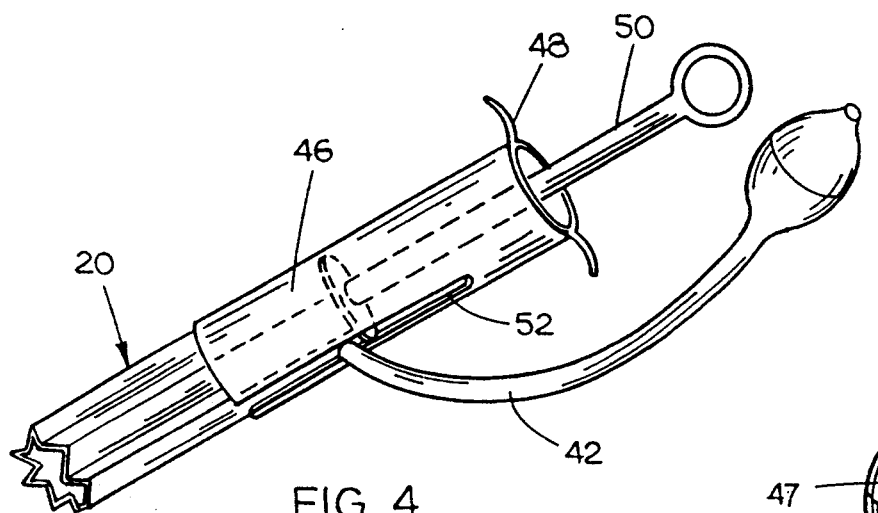
FIG. 4 is a perspective view of the invention prepackaged in an insertion tube.
Figure 5:
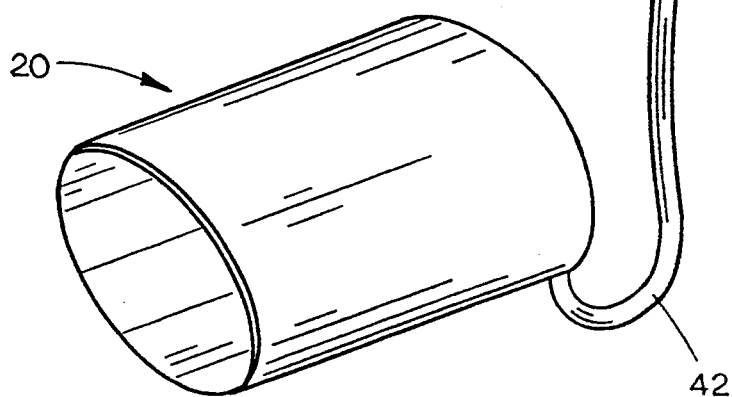
FIG. 5 is a perspective view of the invention removed from the insertion tube and inflated.
Figure 6:
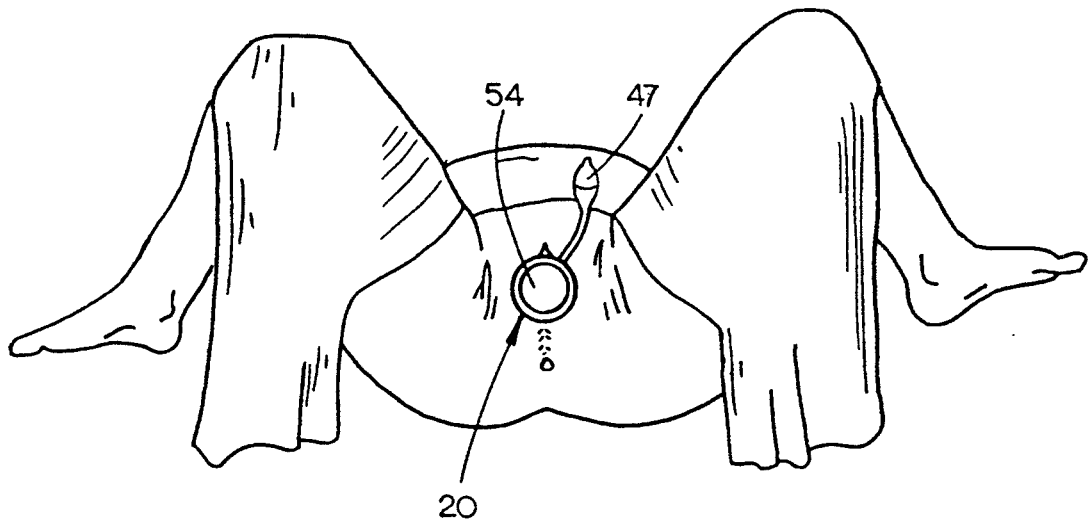
FIG. 6 is a perspective view of a patient with the retractor of FIGS. 4 and 5 operably mounted within the vaginal canal.

Referring now to FIGS. 4–6, retractor 20 may be folded and packaged within a special insertion tube 46, for easy insertion within an incision or orifice, such as the vagina, as shown in FIG. 6. Insertion tube 46 is a hollow cylindrical member with handles 48 at its first end, and a plunger 50 operable therein. A longitudinal slot 52 extends from the second end of tube 46 through which tube 42 of retractor 20 will project. Once ejected from insertion tube 46, retractor 20 is distended utilizing pump 47, as shown in FIGS. 5 and 6. Insertion tube 46 may be easily inserted within the vagina of a patient, because of the narrow diameter of the insertion tube. Plunger 50 (FIG. 4) is utilized to insert the retractor in the desired location, and insertion tube 46 is then discarded. Pump 47 is utilized to distend retractor 20 to provide an opening 54 (FIG. 6) through which the doctor may perform the desired procedure.

Figure 7:
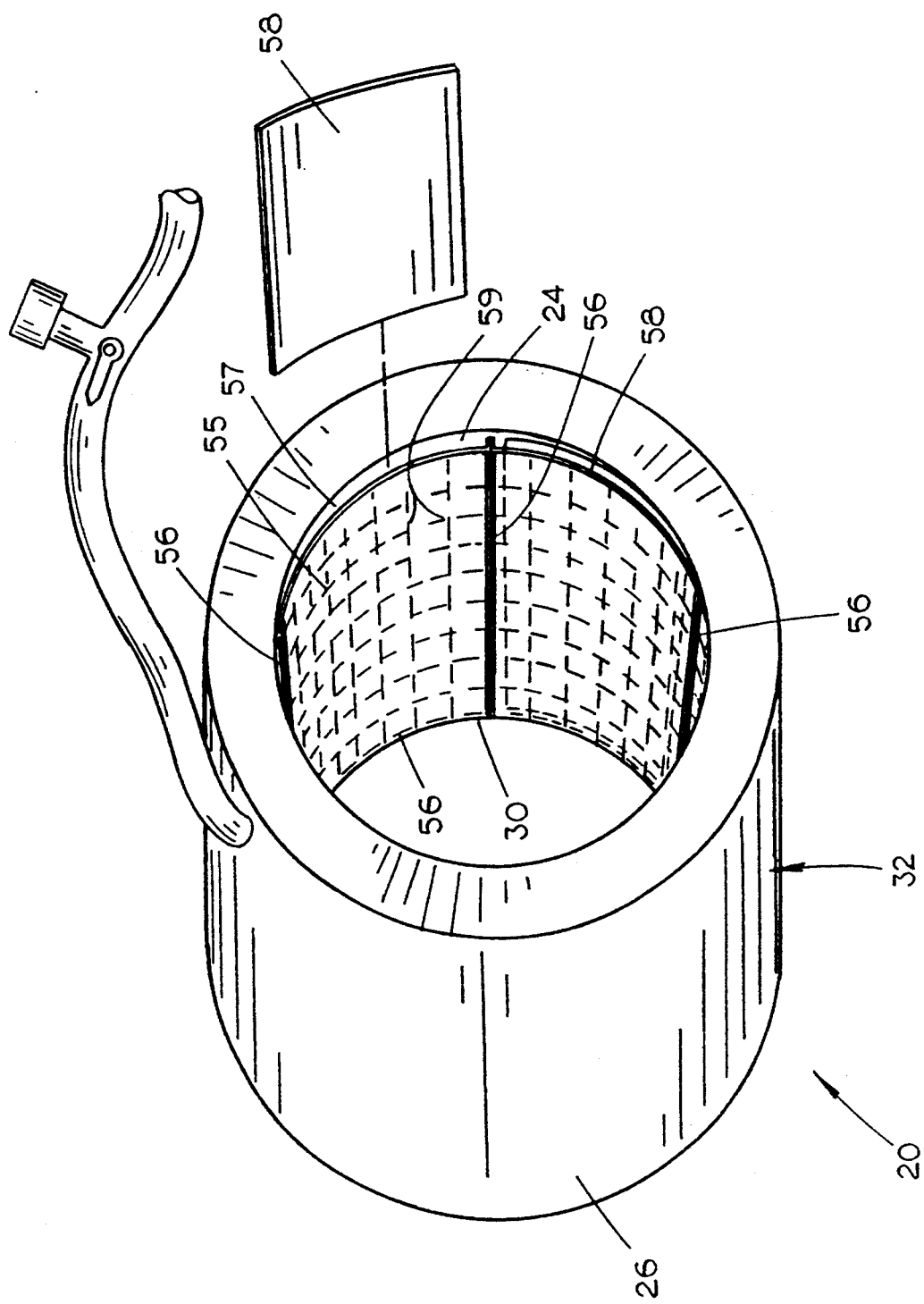
FIG. 7 is a perspective view of the invention with a woven retention matrix and removable puncture-resistant shields.

Referring now to FIG. 7, retractor 20 has a bladder 32 preferably comprised of a material which has elastic properties so as to be expandable to fit the particular incision or opening. In order to restrict the expansion of the bladder to the outer annular wall in a radial direction, a woven fabric is affixed to the externally-directed surface of inner annular wall 24. Woven fabric 55 may be laminated to annular wall 24 so as to prevent all expansion of inner annular wall 24. In such a case, it is preferable that the fabric be formed of a puncture-and incision-resistant material, such that a surgeon working through the central opening of the retractor will not accidentally puncture the bladder 32.

In FIG. 7, woven material 55 is affixed to inner annular wall 24 along a plurality of longitudinal seams 56, extending the longitudinal length of annular wall 24, and along one transverse end around the circumference of inner wall 24 at rearward end 30. Seams 56 form a plurality of pockets 57 into which a puncture- and incision-resistant shield 58 may be removably inserted. It should be noted that woven fabric 55 is preferably formed with interwoven fibers 59 located to form a fiber matrix to prevent stretching of the woven material.

Figure 8:
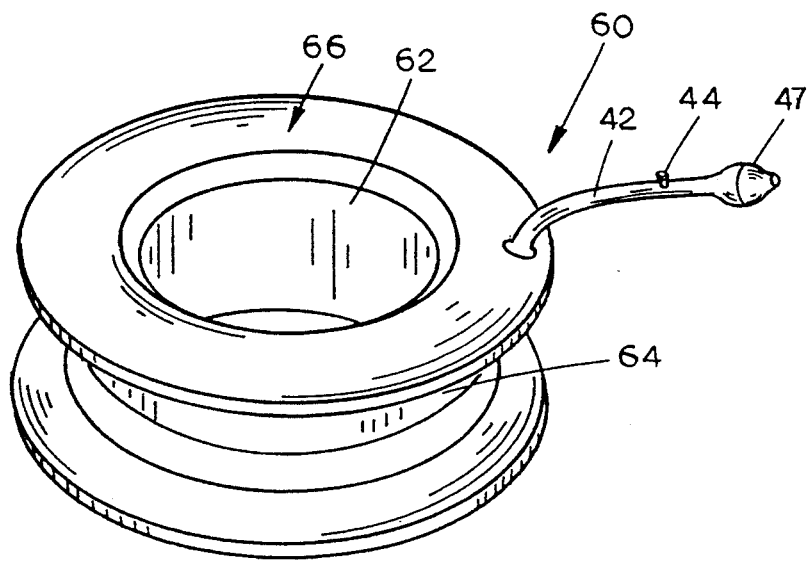
FIG. 8 is a perspective view of a second embodiment of the invention.
Figure 9:
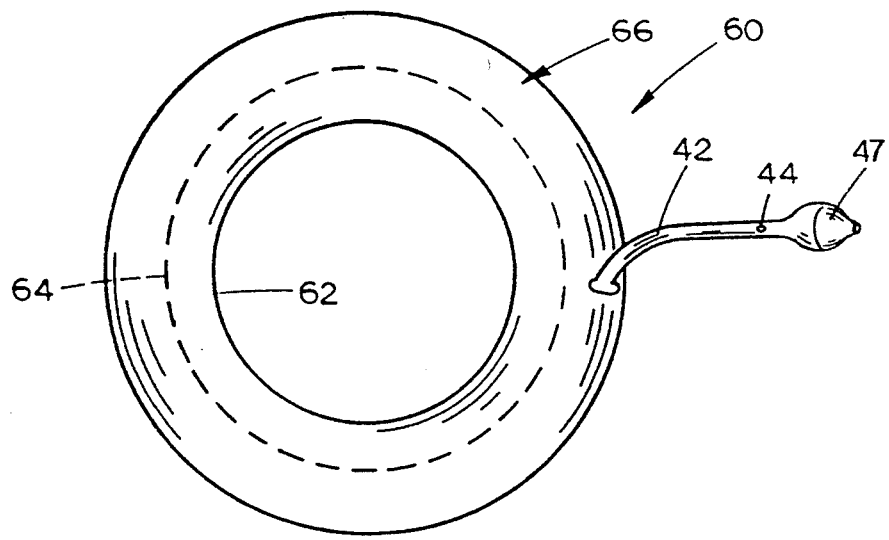
FIG. 9 is a top view of the embodiment of FIG. 7, with a portion broken away for a view of the interior.
Figure 10:
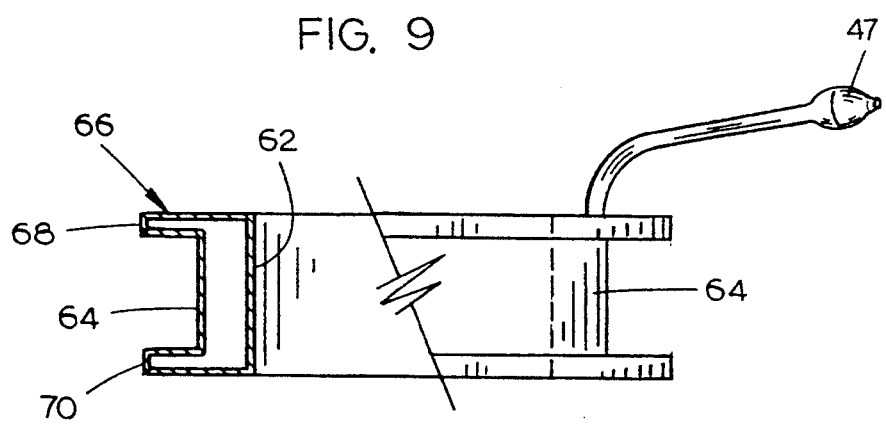
FIG. 10 is a side view of the embodiment of FIG. 7.

Referring now to FIGS. 8–10, a second embodiment of the invention is designated generally at 60 and includes inner and outer annular walls 62 and 64 forming a generally annular bladder 66. Tube 42 extends from, and communicates with the interior of, the bladder to introduce and exhaust air from the bladder. Tube 42 has a valve 44 and pump 47 the same as the first embodiment 20 of the invention. As shown in the broken away portion of FIG. 10, bladder 66 has an upper annular flange portion 68 and a lower annular flange portion 70 which projects radially outwardly from outer annular wall 64, but forms part of the bladder 66.

The second embodiment 60 of the retractor is designed specifically as an epidermis retractor, such that upper and lower flanges 68 and 70 project outwardly over the epidermis, which is sandwiched therebetween against outer wall 64.

Figure 11:
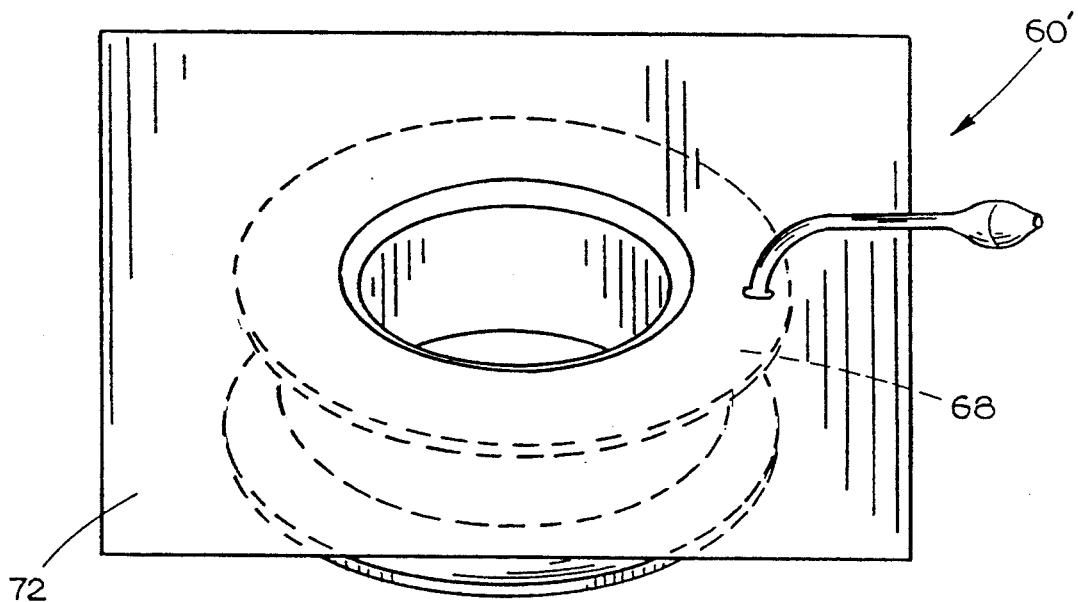
FIG. 11 is a perspective view of a third embodiment of the present invention.
Figure 12:
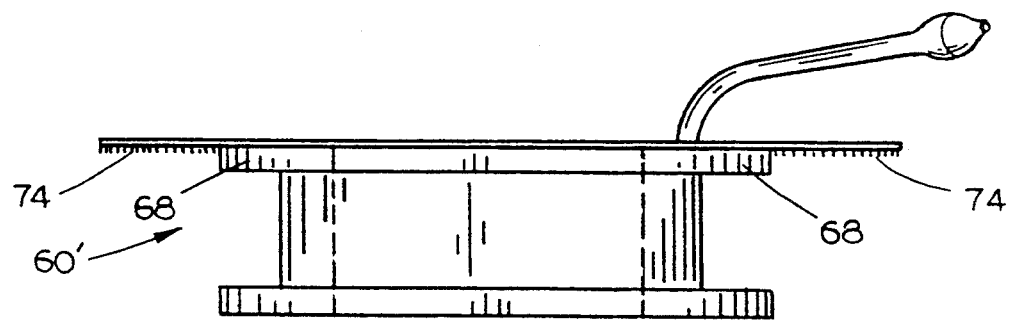
FIG. 12 is a side view of the embodiment of FIG. 10.
Figure 13:
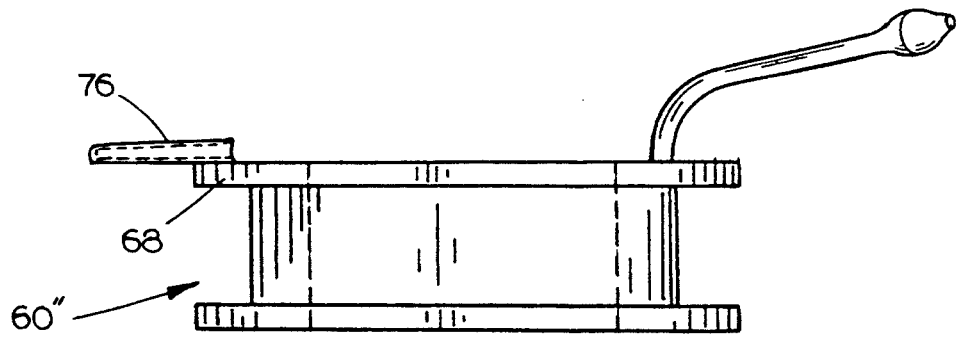
FIG. 13 is a side view of a fourth embodiment of the invention.

A third embodiment of the invention is designated generally at 60' in FIGS. 11 and 12, and is identical to the embodiment of FIG. 8 with the addition of a barrier sheet 72 mounted on upper annular flange 68. Barrier sheet 72 projects radially outwardly from upper flange 68 and will contact the epidermis when retractor 60' is mounted in an incision. An adhesive 74 may be applied to the projecting portion of the barrier sheet to temporarily adhere to the epidermis and maintain the sterile field around the incision.

A fourth embodiment of the invention is designated generally at 60" and is identical to the embodiment of FIG. 8 with the addition of a pocket 76 mounted to the upper flange 68 of the retractor. Pocket 76 is expandable to maintain any organs or viscera within the body which must be moved aside during an operation. Pocket 76 permits the organs or viscera to be maintained in a sterile and non-desicating environment until repositioned within the body.

The foregoing description of the preferred embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

We claim:

1. A fluidly-expandable retractor, comprising:
   a hollow, generally annular member with longitudinal forward and rearward ends, having inner and outer annular walls fluidly sealed together at their forward and rearward ends to form a bladder;
   a generally inelastic fiber matrix laminated to the inner annular wall of said bladder to prevent elastic expansion of said inner annular wall but permit elastic expansion of said outer annular wall; and
   means for distending said bladder fluidly connected to said bladder.

2. The retractor of claim 1, further comprising means for selectively releasing pressure from said bladder.

3. The retractor of claim 1, further comprising means for adjusting the amount of pressure within said bladder.

4. The retractor of claim 1, wherein said outer annular wall is radially elastic, so as to be selectively expandable in diameter.

5. The retractor of claim 1, further comprising a plurality of baffles connecting said inner and outer walls, such that said inner and outer walls are generally concentric.

6. The retractor of claim 1 wherein said member is formed of puncture and incision resistant material.

7. The retractor of claim 1, wherein said inner wall has an internally-directed surface on the interior of said hollow, annular member and an opposing externally-directed surface on the exterior of said annular member, further comprising a layer of puncture and incision resistant material mounted to said externally-directed surface.

8. The retractor of claim 1, wherein said inner wall has an internally-directed surface on the interior of said hollow, annular member and an opposing externally-directed surface on the exterior of said annular member and further comprising a plurality of longitudinally oriented pockets mounted to said externally-directed surface, said pockets having an open forwardly directed end and a closed rearwardly directed end, said pocket open ends adapted to receive inserts of puncture and incision-resistant material.

* * * * *